United States Patent [19]

Engel

[11] Patent Number: 5,056,130

[45] Date of Patent: Oct. 8, 1991

[54] COMPUTERIZED TOMOGRAPHY CALIBRATOR

[75] Inventor: Herbert P. Engel, Melbourne, Fla.

[73] Assignee: The United States of America as represented by the Administrator, National Aeronautics and Space Administration, Washington, D.C.

[21] Appl. No.: 418,364

[22] Filed: Oct. 6, 1989

[51] Int. Cl.$^5$ .............................................. G01D 18/00
[52] U.S. Cl. .................................... 378/207; 378/18; 250/252.1
[58] Field of Search ...................... 378/207, 2, 18, 165, 378/5, 50, 54, 24, 45, 53, 56, 163, 33; 250/252.1 R

[56] References Cited

U.S. PATENT DOCUMENTS

| | | | |
|---|---|---|---|
| 4,055,771 | 10/1977 | Goodenough et al. | 250/305 |
| 4,280,047 | 7/1981 | Enos | 250/252 |
| 4,344,183 | 4/1982 | Jacobson | 378/207 |
| 4,386,850 | 6/1983 | Leahy | 356/243 |
| 4,392,240 | 7/1983 | Tremblay et al. | 378/207 |
| 4,499,375 | 2/1985 | Jaszczak | 250/252.1 |
| 4,549,814 | 10/1985 | Creel et al. | 374/2 |
| 4,551,678 | 11/1985 | Morgan et al. | 324/300 |
| 4,613,819 | 9/1986 | Chui | 324/308 |
| 4,646,334 | 2/1987 | Zerhouni | 378/207 |
| 4,649,561 | 3/1987 | Arnold | 378/207 |

Primary Examiner—Janice A. Howell
Assistant Examiner—Don Wong
Attorney, Agent, or Firm—William J. Sheehan; Harold Wallace Adams; John R. Manning

[57] ABSTRACT

A set of interchangeable pieces comprising a computerized tomography calibrator, and a method of use thereof, permits focusing of a computerized tomographic (CT) system. The interchangeable pieces include a plurality of nestable, generally planar mother rings, adapted for the receipt of planar inserts of predetermined sizes, and of predetermined material densities. The inserts further define openings therein for receipt of plural sub-inserts. All pieces are of known sizes and densities, permitting the assembling of different configurations of materials of known sizes and combinations of densities, for calibration (i.e., focusing) of a computerized tomographic system through variation of operating variables thereof. Rather than serving as a phantom, which is intended to be representative of a particular workpiece to be tested, the set of interchangeable pieces permits simple and easy standardized calibration of a CT system. The calibrator and its related method of use further includes use of air or of particular fluids for filling various openings, as part of a selected configuration of the set of pieces.

26 Claims, 4 Drawing Sheets

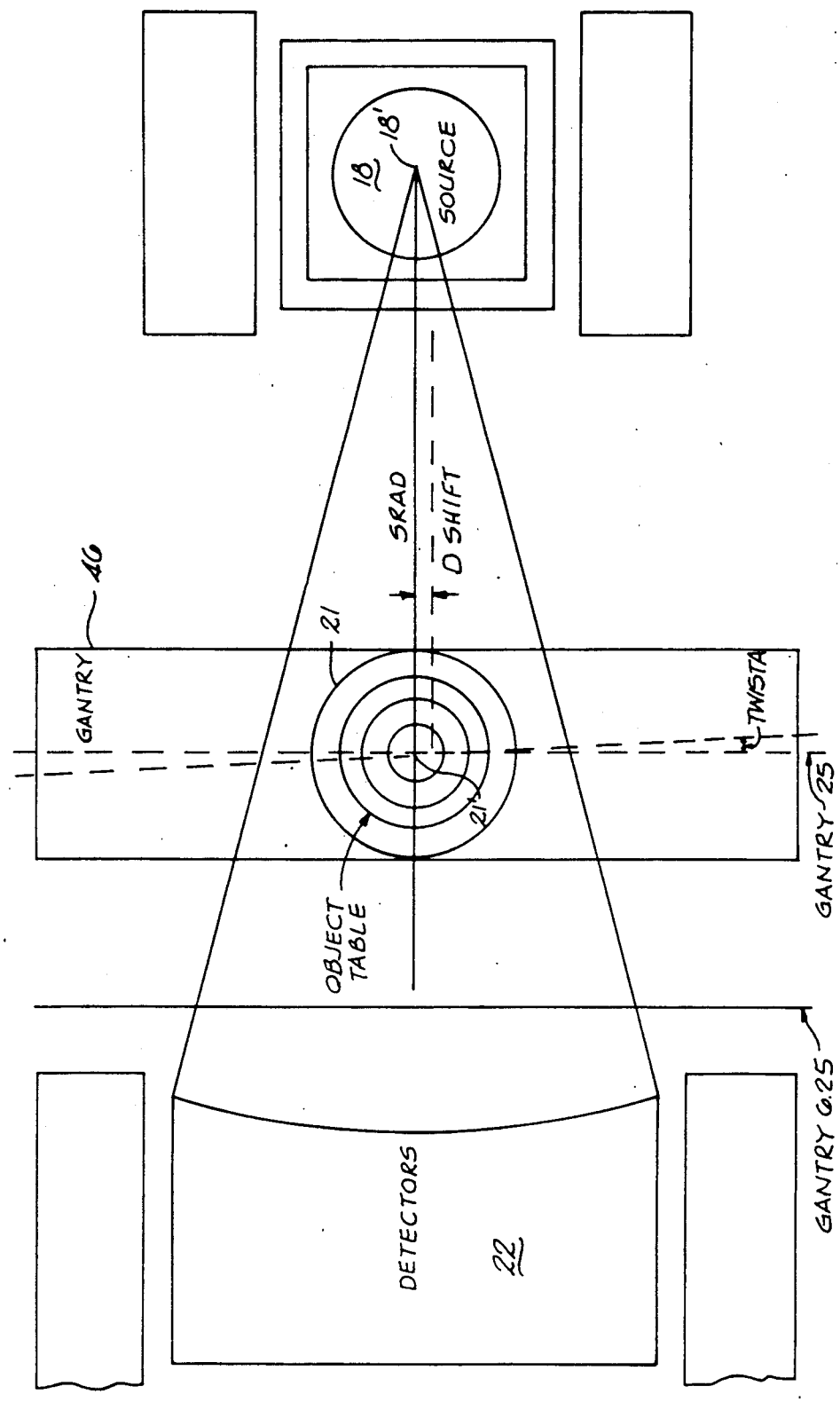

COMPUTERIZED TOMOGRAPHY CALIBRATOR

ORIGIN OF THE INVENTION

The invention described herein was made in performance of work under a NASA contract, and is subject to the provisions of Section 305 of the National Aeronautics and Space Act of 1958, Public Law 85-568 (72 Stat. 435; 42 U.S.C. 2457)

BACKGROUND OF THE INVENTION

The present invention generally relates to a calibrator comprising a set of interchangeable pieces, and related method of use thereof, for calibrating a computerized tomographic system.

With the advent of modern technology, a great variety of scanning and/or imaging techniques have been devised which go far beyond simple optical manipulation of images in the visible light range. Certain of the advanced imaging techniques involve systems which have separate components, such as radiation or exposure sources for exposing an object to be scanned, and various detection devices for detecting resulting interference or the like to the radiation source output, due to the presence, density, etc. of the object to be scanned. Significantly, the interpretation of the detection data may be accomplished substantially in software/hardware combinations, which have settable operating variables which significantly alter the images formed. In other words, a given image generated with software will depend on selection of software variables as much as hardware detection data. Such variables may be several (or more) in number, and may have complex interrelationships, such that their adjustment is not a simple task. Moreover, their adjustment would necessarily vary from one "set-up" to another, just as it is necessary to adjust a camera for focus and the like when going from composing one image to another.

In the case of computerized tomography (CT), a two dimensional picture is created, representative of a plane of interest in a given object. For example, in industrial CT operations, it may be desirable to scan or test a given workpiece for defects. One example would be to check for cracks in a pump or fluid control valve, such as might be used in a space shuttle or in any number of critical applications where an exceedingly high degree of reliability is involved. Nuclear station cooling and control systems is but one further example of such needs.

In such situations, the requisite spatial and contrast resolution and detectability of a CT system will be influenced by various parameters of the scanning or testing to be done. That is, the "focusing" or "aligning" of the CT system will depend on the anticipated size of defects for which the object or workpiece is being examined, relative to the size, thickness, etc. of the workpiece. Since the penetration of various radiation sources is involved, the absolute density and relative densities of the materials involved is also a factor, both in selection of the physical arrangement of the CT system (e.g., selection of exposure source, position of exposure source versus object to be scanned and detector array), as well as selection of the software operating variables. Therefore, the idea and need for a simple and easy CT calibration technique is recognized herewith as fundamentally different from the idea and use of a "phantom", which relates to an exact prototype of the workpiece to be scanned.

The medical profession has made growing use of a Computerized Axial Tomographic (CAT) system, including use of so-called medical phantoms which "mock-up" typical human body dimensions and densities. Such phantoms are limited in their range of object densities, and normally approximate about 1 gm/cc. The needs related to industrial computerized tomographic systems differ in large measure because of significant differences in the objects to be scanned. For example, the range of densities in industrial workpieces to be scanned can easily cover about 0 gm/cc to about 10 gm/cc. Also, size is a consideration, wherefore industrial workpieces requiring examination can easily involve objects in excess of five feet by six feet in measurement, and weighing over one ton. Normally, the typical medical targets would not have such a range of size and weights.

Some industrial phantoms have been developed to either mock-up a unique or specific industrial device, such as a rocket motor, or have been developed to test system detectability and so-called contrast resolution over relatively narrow ranges of size and density. Examples of such phantoms are the Sieman's Star, the NSF (National Science Foundation) phantom, and certain rocket motor phantoms. Another example generally is the AAPM (medical) phantom. Such phantoms do not typically have uniform geometric features, and do not permit significant variation in the ranges of size and densities which may be provided. For example, the AAPM phantom is a generally plastic structure permitting focus and resolution only in that given density. The NSF phantom provides a series of smaller and smaller plates, but with no significant degree of density variation. Also, the intended purpose of such structures is primarily to be a mock-up for a particular device or structure to be scanned, rather than to aid in the general calibration of the CT system (whether medical or industrial in character).

SUMMARY OF THE INVENTION

The present invention generally recognizes and addresses such needs in relation to a calibrator for a computerized tomography (CT) system, and the various drawbacks of prior art phantom devices and methods. Accordingly, it is one general object of this invention to provide a calibrator and related method of use thereof which will simply and easily provide for global standardized calibration procedures for computerized tomography systems. A more particular object is to provide a set of interchangeable pieces of known sizes and densities, which in varying combinations thereof will permit calibration of a CT system for optimum operation with a variety of given set-ups.

Another general object is to provide a functional device and related method of use for testing the overall detection, resolution, and dimensional measurement capabilities of CT systems. It is also a present object to satisfy the need to periodically calibrate CT systems to insure that they maintain a desired degree of analytical consistency.

It is a further broader object of this invention to provide a -single computerized tomography calibrator with the ability to adequately characterize all CT system limitations for conceivable CT scanning problems, regardless of the nature of the mechanical item to be scanned. More particularly, it is an object to provide items of varying densities and material thicknesses or combinations thereof, adapted for calibration purposes.

It is a still further general object of this invention to provide a calibrator which may be used with all present and future industrial (as well as medical) computerized tomography facilities.

It is a more particular object to provide a set of interchangeable pieces (preferably generally planar in nature) to permit their assembly in a given, known configuration of sizes and varying material densities in an intended plane to be scanned with a CT system. It is a further object to provide such a set of interchangeable pieces, which may also be stacked in various planar configurations for determining slice plane thickness, resolution, and adjacency of the CT system. Another more specific object is to provide such a set of interchangeable pieces, having different given densities over a wide range, generally from about 0 gm/cc to about 10 gm/cc, to facilitate calibration for most industrial applications, as well as medical applications.

It is also a general object of this invention to provide a corresponding method of use for an interchangeable set of calibrator pieces provided in accordance with this invention. A more specific aspect is to provide such a method which includes use of air and various non-corrosive fluids for filling openings in the set of interchangeable pieces, to further permit variation for density contrast tests, or the like.

Summarized in another way, it is a broad, general object of this invention to provide a computer tomography system calibrator which is simple, but yet capable of broad ranges of varying size and combinations of different density materials for characterizing CT system capabilities. Use of such a calibrator results in the establishment of correct system software/hardware variables for all possible CT system configurations, and therefore facilitates the production of optimum scanning conditions for all varieties of objects to be examined. Once a unique subject to be scanned is selected, use of the calibrator and its corresponding method of use, permits the CT system to be placed in optimum data acquisition conditions.

Additional objects and advantages of the invention are set forth, or will be apparent to those of ordinary skill in the art, from the detailed description that follows. Also, it should be appreciated that modifications and variations to the specific illustrated and discussed features hereof, as well as steps of the incorporated methods, may be practiced in various embodiments and methods of this invention without departing from the spirit and scope thereof, by virtue of present reference thereto. Such variations may include, but are not limited to, substitution of equivalent means, features or steps for those shown, described or suggested, and the reversal of various parts or steps, or the like.

Still further, it is to be understood that different embodiments, as well as different presently preferred embodiments (both as to structures and methods) of the present invention may include various combinations of presently disclosed features, steps, or their equivalents.

One such exemplary embodiment of the present invention relates to an industrial computerized tomography calibrator, comprising a plurality of nestable, planar rings, removably received relative one another, and each respectively defined at least one opening of predetermined size situated therein, between their respective inside and outside diameters, and a plurality of planar inserts adapted to fit and be removably received in the predetermined-size openings. With such a calibrator, the rings and inserts are preferably comprised of selected materials having known densities and dimensions. With such features, different combinations of the rings and inserts may be provided to establish predetermined density and dimensional material relationships in a given plane, for use in calibrating an industrial computer tomography system.

Another present exemplary embodiment concerns a device to aid in the image focusing of a computer tomography system having computer means with adjustable variables for generating an image from exposure detection data gathered with such system. The device preferably includes a plurality of generally planar mother block means, of predetermined size, thickness, and density. Such mother block means are adapted to be removably associated with one another, and to have primary openings therein, for establishing a dimensionally known planar pattern of such primary openings. The device further includes a plurality of generally planar insert means, of predetermined size, thickness, and density, and adapted to be removably received in the mother block means primary openings, for generally filling same. With such a device, selected planar configurations of varying combinations of known sizes and densities may be provided, to permit adjustment of the system computer means variables for optimum image detection and image contrast and spatial resolution.

With each of the foregoing embodiments, the inserts or insert means may be provided with further openings (i.e., secondary openings) or the selected receipt of sub-inserts or secondary inserts, also preferably of predetermined size, thickness, and density.

Yet another construction comprising an exemplary embodiment of this invention includes a set of interchangeable pieces for use in focusing the level of detectability and the contrast and spatial resolution of a computer tomography system having settable variables for adjusting effective image detectability and resolution of the system. Such set of interchangeable pieces includes a plurality of nestable, generally planar mother rings. Each ring has at least one predetermined opening within its respective circumference, and is adapted for the receipt of planar inserts of predetermined sizes in such openings. The pieces further include a plurality of removable planar inserts adapted to be received in the mother ring openings. Mother rings and inserts are preferably comprised of materials having known densities, whereby different configurations of materials of known sizes and combinations of densities may be provided generally in a given plane to be scanned with the computer tomography system, for focusing of such system through adjustment of the settable variables thereof.

The present invention also generally relates to a method of focusing a computer tomography system, such as of the type having a radiation source for exposing an object to be scanned, an exposure support surface for supporting an object to be scanned, detector means for detecting scan information, and computer means with operating variables for processing scan information into images. One exemplary method in accordance with this invention for use with such a system includes the steps of: providing a set of interchangeable pieces, each piece comprising a given material of generally known density and dimensions, such set of pieces including a plurality of nestable mother rings, and inserts for removable selected association with each of the mother rings; assembling at least certain of the pieces into a given configuration thereof, with such configuration being received on the computer tomography system exposure support surface; operating the computer tomography system for exposing the assembled configuration of pieces; and processing detected scan information into images, including adjusting the computer means operating variables so as to obtain optimum image quality based on the known configuration of certain densities and dimensions provided with the assembled pieces.

Those of ordinary skill in the art will better appreciate the features and aspects of such embodiments, methods, and others, upon review of the remainder of this specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures, in which:

FIG. 4 is a top elevational view of a computer tomography set-up, to which particular reference is made hereinafter in connection with disclosing the present methodology.

Figure 1:
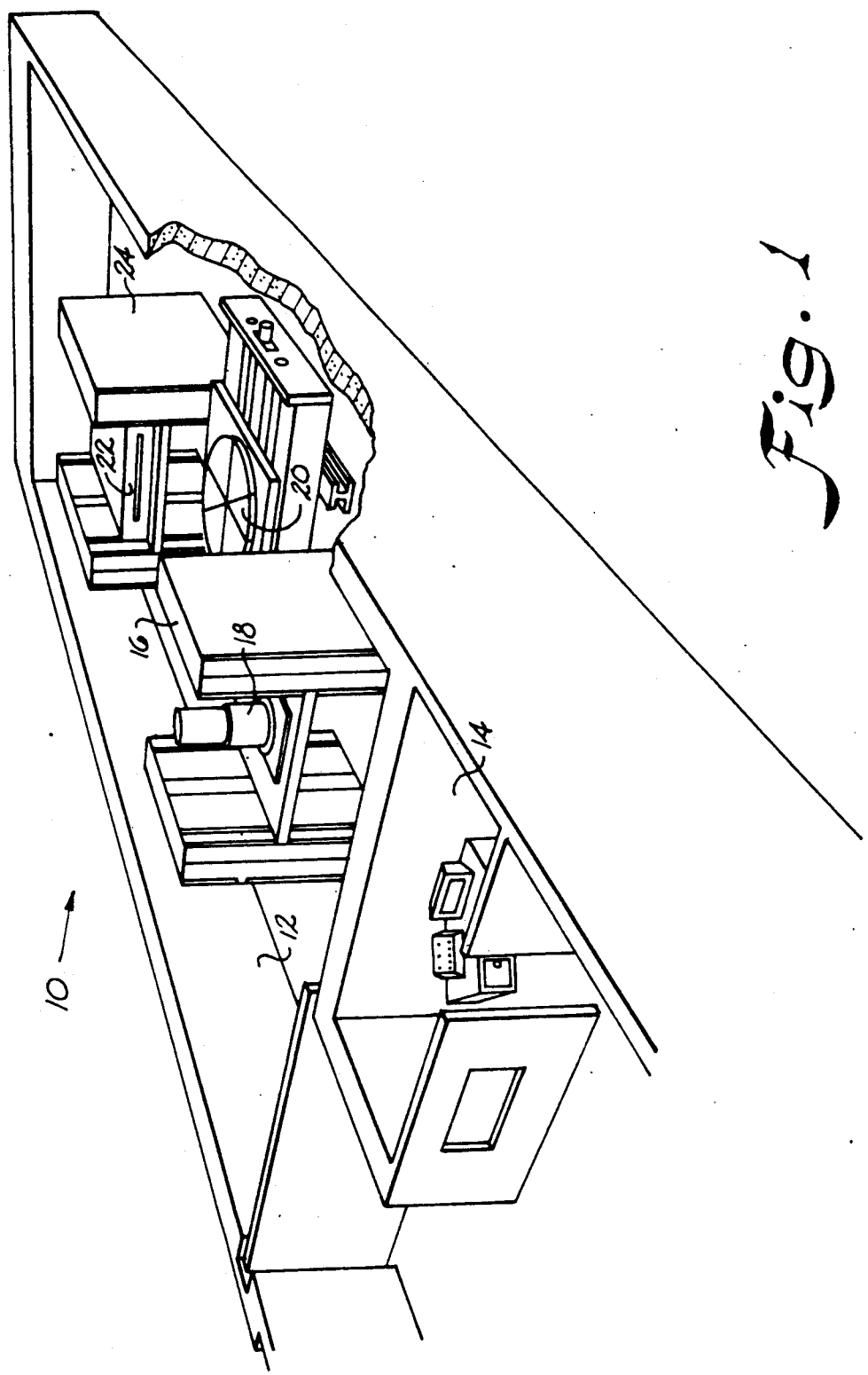
FIG. 1 is a perspective view of a computer tomography facility, such as may be used with a calibrator in accordance with this invention, and in accordance with methodology herewith.

Repeat use of reference characters throughout the present specification and appended drawings is intended to represent same or analogous features or elements of the invention.

DETAILED DESCRIPTION OF THE PREFERRED EMBODIMENTS

Those of ordinary skill in the art should understand and appreciate that the present invention may be practiced with many different computerized tomography (CT) systems, both industrial and medical. For purposes of example and discussion only, FIG. 1 herewith represents a computer tomography facility at Kennedy Space Center, NASA, in Florida. In particular, the facility makes use of a Model 201 CITA (Computed Industrial Tomographic Analyzer) made by Scientific Measurement Systems, Inc. of 2209 Donley Drive, Austin, Tex., 78758.

The SMS Model 201 is generally evolved from the same technology as used in medical CAT Scan techniques, for nondestructive evaluation and for providing data acquisition not generally available with conventional radiographic methods. A facility such as in present FIG. 1 provides for both a digital radiograph and a cross-sectional slice of the item or workpiece under investigation. The facility 10 is enclosed in a shielded exposure cell 12, and has a separate control and computer room 14. An exposure source tower 16 may be operated with an interchangeable source 18. Various sources may be practiced, including a 20 to 100 curie cobalt-60 source, or a variable 420 kV X-ray source. As understood by those of ordinary skill in the art, a workpiece, such as a control valve or pump, or the like, is supported on a turntable translator assembly 20 for scanning. A detector array 22 is supported with a detector tower 24.

In the exemplary facility 10 of present FIG. 1 the turntable is particularly adapted for potential use with a variety of components supporting launch activities. An object weighing up to two thousand pounds and measuring up to six feet in height and five feet in width can be supported on turntable 20, and thus examined with facility 10. The interchangeable exposure sources provide penetration capabilities from thin, low density materials up to a steel equivalent thickness of approximately eight to ten inches.

Examinations may be conducted for a variety of workpieces, such as evaluation of critical components for the presence of packing material, weld integrity, component location-dimensional measurements, and changes in material density. Use of a facility such as that in FIG. 1 may be particularly adapted to support Kennedy Space Center operational and research development activities, but may be used to investigate other computer tomography applications in other specific problem areas. The general operation of a CT system is well known to those of ordinary skill in the art, and hence need not be discussed herein. Specific operation of such a system, in accordance with present methodology, is discussed below with reference to FIG. 4.

Those of ordinary skill in the art will appreciate that numerous variations may be practiced relative to the specific exemplary embodiment disclosed hereinafter. One such embodiment preferably comprises a set of interchangeable pieces including planar, nestable mother block means and planar inserts or insert means therefor.

Figure 2:
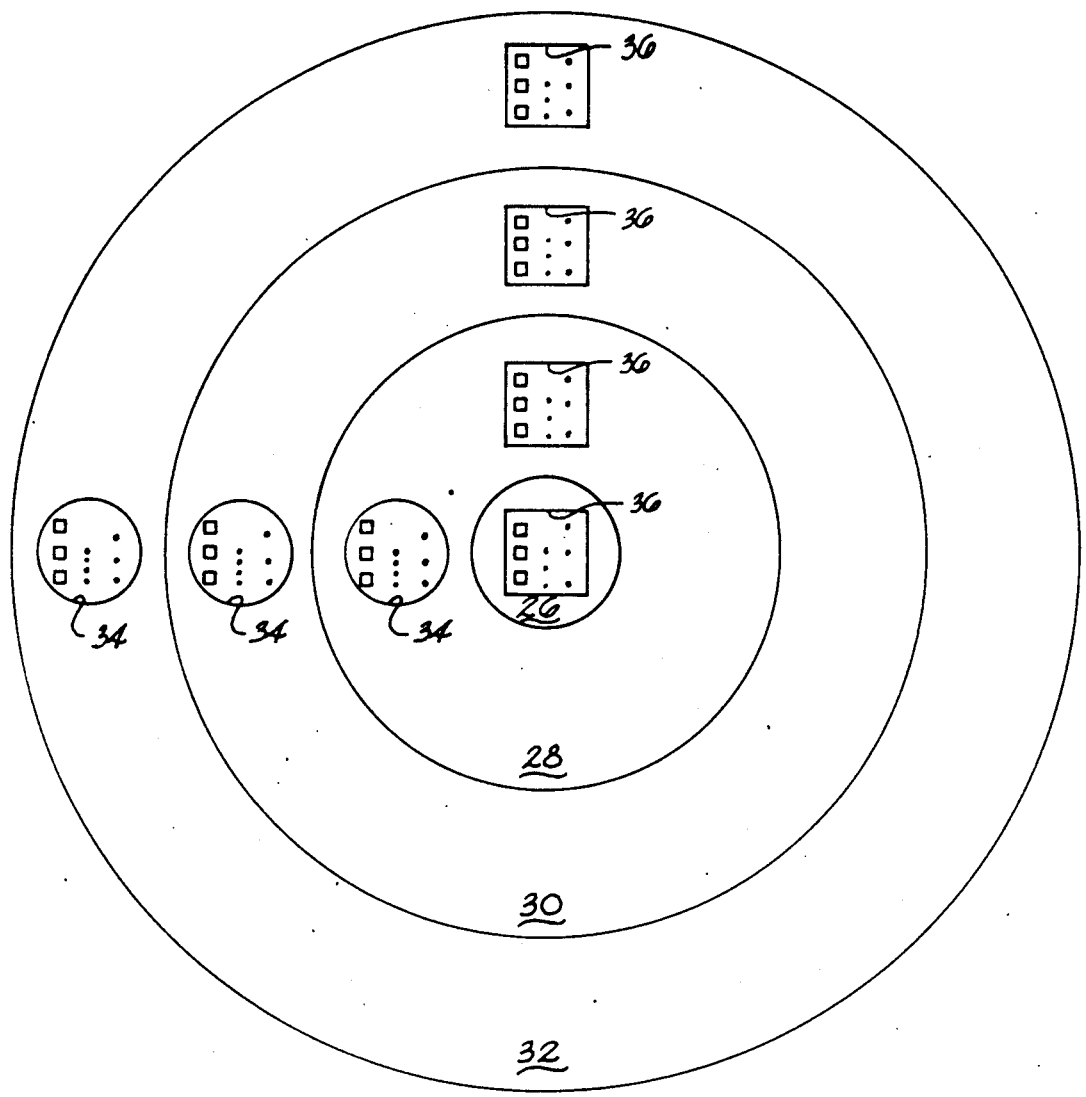
FIG. 2 is a top elevational view of an embodiment of a calibrator in accordance with the present invention, showing an exemplary assembled set of interchangeable pieces as disclosed herewith.

In the exemplary embodiment presently illustrated in the top elevational view of FIG. 2, the mother block means comprise mother rings or planar rings 26, 28, 30, and 32. Each ring has at least one predetermined opening within its respective circumference for receipt of inserts means therein. Preferably there are a total of four mother rings, with the center ring 26 substantially comprising a disc, while the remainder comprise annular, concentric members which are preferably about two-inches wide, and nested, varying from a maximum diameter of about fourteen inches to a central ring of about two inches in diameter. The mother rings are preferably planar, with a thickness of about 10 mm, with a predetermined size, shape, and density of material.

The insert means are preferably either circular, such as the planar inserts 34, or are square such as the planar inserts 36. The mother rings have primary openings within the circumference thereof, for receipt of either one or both of the insert means in a predetermined, fixed location therein. The rings and inserts fit generally loosely with respect to one another, so as to be readily interchangeable, as to both orientation and material type. The inserts (of either type) removably receive sub-inserts as discussed below. For the sake of clarity, such sub-inserts are represented in FIG. 2, but labeled and discussed in conjunction with enlarged FIG. 3.

Figure 3:
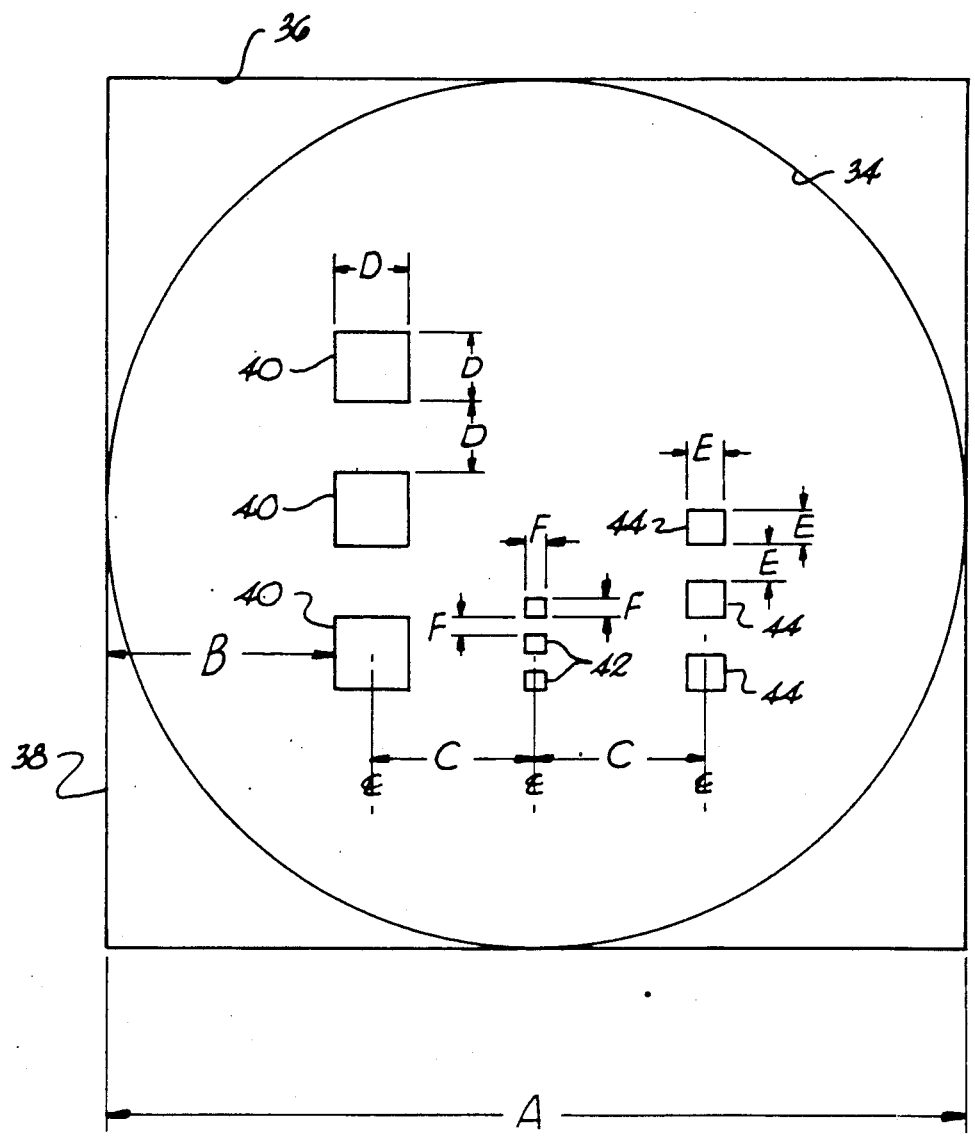
FIG. 3 is a top elevational view of an exemplary removable insert in accordance with this invention, combined with removable sub-inserts for use therewith.

FIG. 3 represents a top perspective view of insert means in accordance with the present invention, such as circular insert means 34 or square insert means 36. As illustrated in FIG. 3, each of the insert means further define sub-openings or secondary openings for the receipt of sub-inserts or secondary inserts therein. Similar to the planar mother blocks or rings, the insert means and sub-inserts are preferably planar, and have fixed dimensions and opening locations, and a known material density. As will be discussed hereinafter, preferably the sub-openings and sub-inserts have generally corresponding dimensions, with the sub-openings being slightly larger to facilitate removal of the interchangeable sub-inserts. The fixed, relative locations may be determined by specifying values in a given embodiment of the invention for variable dimensions A through F, discussed hereinafter with reference to present FIG. 3.

Dimension A, the side of each square inserts means 36, is preferably about 25 mm, meaning that the radius of a corresponding circular insert means 34 is approximately 12.5 mm. The distance B from a side wall 38 of insert means 36 to a side wall of sub-insert 40 is preferably approximately 6.75 mm. The centerline of sub-inserts 40 is separated from the centerline of sub-inserts 42 by distance "C", which is the same distance as between the centerline of sub-inserts 42 and that of sub-inserts 44. The distance C is preferably about 5 mm.

There are preferably nine sub-inserts or secondary inserts, grouped by different sizes in sets of three. For each given set, the distance on each side of the square sub-insert as well as the distance between its adjacent sub-insert of like kind, are all equal. As shown, these respective distances for sub-inserts 40, 44, and 42, are "D", "E", and "F", respectively. The distance D is preferably about 2 mm, while the distance E is preferably about 1 mm, and the distance F is about 0.5 mm. All corners on such sub-inserts are preferably rounded with radii of about 0.0035 inches to about 0.004 inches.

A total of seventy-four pieces comprise a complete set of interchangeable pieces in accordance with one embodiment of the invention, and includes four mother rings, seven planar inserts, and sixty-three sub-inserts. The pieces may be made from a variety of materials, such as aluminum, copper, stainless steel (e.g., SS-304), carbon, and carbon composites. If three separate, complete sets are made, such as from aluminum, copper, and stainless steel, two hundred twenty-two interchangeable parts will be available for combining different density materials in testing the detectability and resolving power of the CT system, in accordance with the present invention. The respective components or pieces may also be stacked for determining slice plane thickness, resolution, and adjacency, as discussed below. The machining is probably best performed using electro-discharge or $CO_2$-laser techniques, particularly in connection with formation of the sub-inserts measuring 0.5 mm on a side, and their corresponding openings into which they are received. "Square" corner cuts should have a maximum radius of 0.005 inches. Primary opening/insert and secondary opening/sub-insert relative tolerances preferably should allow gravity dropout of the components, all of which greatly facilitates handling and use of the calibrator in accordance with this invention.

The density range of a set including aluminum material through copper is approximately 2.7 gm/cc through 8.7 gm/cc, respectively. Other sets may be manufactured to cover all conceivable density ranges, in accordance with this invention, for which an industrial CT system would be required to scan. Use of stainless steel materials permits an intermediate density range material (intermediate relative to a range generally from 0 to about 10 gm/cc).

In accordance with the present invention, intentional omission of an insert or sub-insert in a respective primary or secondary opening is equivalent to the use of air as an insert or sub-insert (with a near 0 gm/cc density). Also, preferably non-corrosive fluids may be entrapped in various primary or secondary openings, and should be of known density to further facilitate the creation of various combinations of parts to provide differing density combinations in the field of a CT scan plane view for focusing or refinement of CT system operations.

Preferably, a nominal thickness of 10 mm is utilized for all pieces, though different thicknesses may be practiced. The 10 mm thickness is preferred because it typically corresponds with the maximum thickness of a slice plane which is scanned with the CT system, and engages well the usual CT slice plane of 1 mm.

Methods of use of the present calibrator, the components of which are represented in FIGS. 2 and 3, generally involve placement of the calibrator, parts thereof, or combinations of parts to provide differing density combinations in the field of CT scan plane view. The CT system is then operated through the CT manufacturer's parameter input range in order to optimize detectability and resolution of the features provided by the calibrator configuration. The calibrator configuration may include stacked members oriented differently about their axis, scanned near the interface thereof, in order to determine the effective height of the slice plane. Dimensions and materials utilized in accordance with the present calibrator may be varied in order to suit specific calibration requirements; however, it is preferred that the dimensions of the subject calibrator will provide features of a size range that will test and calibrate any known industrial CT system.

In general, a calibrator set as represented in present FIGS. 2 and 3 serves as a computerized tomography calibrator in general, and is particularly useful as an industrial computerized tomography calibrator comprising a device to aid in the image focusing of a computer tomography system having computer means with adjustable variables for generating an image from exposure detection data gathered with such system. As referenced above, FIG. 1 illustrates such a system 10, having computer means located in the control/computer room 14 thereof, which receives input or exposure detection data gathered with a detector array 22.

With use of the present calibrator, different combinations of rings and inserts may be provided to establish predetermined density and dimensional material relationships in a given plane, for use in calibrating the industrial CT system. Thought of another way, the calibrator components may be placed in selected planar configurations of varying combinations of known sizes and densities, to permit adjustment of the system computer means variables for optimum image detection and image contrast and spatial resolution. More particularly, the present invention is useful with a method of focusing a computer tomography system of the type having a radiation source for exposing an object to be scanned, an exposure support surface for supporting an object to be scanned, detector means for detecting scan information, and computer means with operating variables for processing scan information into images. Such is precisely as represented in present FIG. 1, as discussed above.

In such method, generally, a set of interchangeable pieces such as discussed above is provided, and then at least certain of such pieces are assembled in a given configuration, supported on the system exposure support surface. Thereafter, the computer tomography system is operated for exposing the assembled configuration of pieces, and the detected scan information is processed into images. During the course of such processing, different operating variables of the computer means may be adjusted so as to obtain optimum image quality based on the known configuration of certain densities and dimensions provided with the assembled pieces. As referenced above, such assembly of pieces includes and makes use of air and/or non-corrosive fluids such as may be entrapped with tape or the like within primary or secondary openings of the calibrator.

The following discussion relates more directly to methodology in accordance with the present invention, and makes reference to present FIG. 4. FIG. 4 is a generally top elevational view of the primary operative components in a CT system, and are representative of source 18, object support table 21, and detectors 22. While various set-ups will differ from one installation to another, the use of the basic components of a CT system as discussed herein is regarded as universally applicable to all CT systems.

Further represented in present FIG. 4 is a gantry 46, which preferably forms a portion of the turntable translator assembly 20 represented in present FIG. 1. The apparent purpose of such gantry is to permit desired manipulation and positioning of the object to be scanned, whether a workpiece, a phantom mock-up of such workpiece, or a calibrator in accordance with the present invention. Gantry location may be varied and given arbitrary values for the sake of reference, such as the exemplary alternative gantry positions labeled "GANTRY 6.25" and GANTRY 25" in FIG. 4.

The term "calibrator" is deemed a more appropriate reference to the subject matter of the present invention rather than the term "phantom", since a phantom is generally a unique device, while the present calibrator permits characterization of all potential variations of objects that can be scanned with a CT system. The present calibrator permits a user to establish correct system software/hardware variables for all possible CT system configurations, and therefore produce optimum scanning conditions for all varieties of objects examined. A CT system may be placed in optimum data acquisition conditions based on criteria established with a given calibrator configuration. A very wide range of density and dimensional variations or assembled combinations may be achieved with the multiple interchangeable parts of such calibrator, specific examples of which various assemblies need not be shown here for a full understanding and appreciation thereof by those of ordinary skill in the art in light of this disclosure taken as a whole.

Optimum operation of a CT system is significantly based upon proper adjustment and alignment of system hardware parameters to those of the calculational software. In other words, various dimensional conditions and aspects of the hardware system must be accounted for in the software which is used to actually generate an image based on the detection data from detectors 22. Many "adjustable" variables are encountered in pre-system operation. Various acronyms used herein for indicated variables are arbitrarily selected, and are used as a matter of convenience as having already been adopted in the vocabulary associated with the NASA facility 10. The acronyms themselves do not expressly limit this invention.

First, the source type, whether x-ray or cobalt-60, must be selected. Also, the subsequent source to detector vertical alignment (VSHFT) must be selected. Next, collimator settings of the source must be established, which relate to beam height and angle, e.g., 3 or 4 mm by 36 degrees. Also, just as collimator settings of the source must be established, collimator settings for the detector must be established (i.e., width and height detection adjustments must be made). Such adjustments generally range from about 0.5 mm (or less) to 4 mm and up to 20 mm high. A typical relatively "high" resolution setting is 1 mm wide by 2 mm high. With the particular SMS Model 201-CITA used at the NASA facility, "slice" thickness is nominally about 1 mm at the plane of the tomogram. This is not normally regarded as an adjustable parameter, even though the data collected with the detectors will vary slightly above and below the plane of interest due to changes in the detector collimator effecting slice thicknesses of about one-half the detector collimator height. Since the chief object of a CT scan is two-dimensioned datum, variations in "slice" thickness is of somewhat questionable value or utility. If a very "quick" or brief imaging is desired, a limited picture height, digital, radiograph might be made over a relatively "thicker" plane of interest.

The next variable which can be adjusted in a given system setup is the distance from the source to the center of rotation (SRAD). As shown in FIG. 4, SRAD is the straight line distance from the center 18' of source 18 to the center 21' of rotary object table 21.

Other "variables" are a result of various hardware and software interface and interplay characteristics. For example, the geometrical lateral "shift" of the SRAD between the system hardware and software is referred to as DSHFT, and is represented in present FIG. 4 by the dotted line marked DSHFT, which is offset from the solid line SRAD. Another effective variable is a slight skew angle from 90 degrees between the gantry travel line and SRAD, which angle is referred to as TWISTA. See FIG. 4.

Of the above-mentioned variables, methods of use involving the present calibrator primarily are intended to permit adjustment of the effective image detectability and of the system resolution (both contrast and spatial). The specific variables mentioned above which resultingly are adjusted in accordance with the present methodologies are primarily SRAD, DSHFT, and TWISTA.

VSHFT, since it aligns the source beam to the detector window, must as a practical matter be set for each source before data acquisition is commenced. This is very easily achieved through available driver units, and seldom needs any adjustment. In fact, adjustment of VSHFT may be made automatic as part of the set-up operation, by monitoring the specific source being utilized.

Since the primary adjustments involved with the present invention relate to manipulation of software variables which are used in the computer means associated with control/computer room 14, SRAD, DSHFT, and TWISTA can actually be changed after data acquisition, such as during the data convolution of the transmission data file. This is analogous to being able to focus a camera after the picture has been taken, and thus provides for a very powerful calibrator tool and methodology.

In accordance with this invention, computers associated with the task of developing images from the detection data may be set up for iterative processes and subsequent picture production for each variable change, normally with a simple command language program. Pictures (i.e., slice plane images) of the calibrator from the various iterations may then be examined at a later time, and compared for determining optimum detectability and resolution.

In other words, for a given gantry setting between the source and the detector, only one CT "data acquisition run" is necessary. Fine tuning or adjustment of the SRAD, DSHFT, and TWISTA variables is thus done at a later time "after-the-fact". Of course, this approach is primarily effective where the variables have been closely estimated for a given gantry position. Since operation of the computer means results in a visual image, whether produced on a screen, or in a photograph, or in a hardcopy form, or the like, it may be reviewed and considered by a control operator for judging optimum settings. Since the different variable settings may be associated with the different images, the best settings are readily perceived.

Further and various methodologies may be used in accordance with the present invention, or in accordance with a calibrator embodied in accordance with this invention. For example, selecting the sizes of the inserts and sub-inserts, as well as the given mother rings or the like, may be made based on the relative dimensions thereof in relation to the size of an intended object to be scanned with this system and the anticipated size of defects in such intended object. For example, generally, the dimensions of the largest mother ring may be selected at least as large as the intended object to be scanned (at least in the target scan plane of such object), and the dimensions of the smallest sub-insert may be selected so as to be no larger than the smallest anticipated defect in the intended object. Such bracketing of relative dimensions, together with accompanying appropriate selection of different density materials, will yield a superior approach to appropriately focusing a CT system for a particular task.

As referenced above, the interchangeable pieces may be stacked in accordance with a further aspect of this invention, to permit testing of the level of system rejection of scan information from adjacent planar locations (i.e., outside the intended given plane to be scanned). Still further, a test piece of known size and density may be placed on the computer tomography system exposure support surface, outside the assembled configuration of interchangeable pieces, to permit the monitoring of drift in relative density indications from one processed image to another. Such drift is monitored by simply not changing the test piece (or at least, not changing its density) between the formation of respective images. Such an approach also permits "detected" density information to be compared against "textbook" density values.

As also referenced above, the selective entrapment of air or non-corrosive fluids of known density in predetermined areas of the assembled configuration adds to the variety in available configurations of known density and location of materials to be scanned.

Selection and use of particular geometric shapes also may be used in particular fashion by the operator, for either selectively avoiding or generating artifacts. Selective use of a rectangular shape, which for example stimulates artifacts generation, permits simultaneous testing of geometry and density resolution with a single opening/insert pair. Of course, if all openings and sub-openings are filled with inserts and sub-inserts, respectively, in a given configuration of the calibrator, and all pieces of the same density, it should be apparent to those of ordinary skill in the art that the relatively close tolerances of the respective openings and their corresponding inserts (even though removable therefrom) will appear collectively as though a solid mass of fixed density material in the given plane is scanned. Thus, it is the variations in configurations, omissions, use of air or non-corrosive fluids, or other differing density materials and the like, which yields up the different assemblies of density and dimensional characteristics which best aid in the focusing or alignment of a given CT system.

It should also be appreciated and understood by those of ordinary skill in the art that the present calibrator, as well as the present methodology generally, will be operative with different types of machines, including those with different operating variables (whether medical or industrial CT systems). The primary intent of the calibrator and its use is in focusing such a CT system, rather than serving as a mock-up or phantom for a specific workpiece to be scanned. Hence, the need for a prototype or phantom (i.e., a true or industrial phantom in the classic sense) is not necessarily eliminated.

It is expected that those of ordinary skill in the art will apply their knowledge of materials, as well as input parameters from the workpiece to be scanned, in establishing parameters for use in selecting a given calibrator configuration. Such leeway and application of knowledge in practice of the present invention is expected, if not in fact required, due to the interrelated nature of the many variables relating to the level of detectability, and contrast and spatial resolution, as well as the wide applicability of the present invention. Such three characteristics are highly sensitive to set-up changes. The level of detectability of a system varies with the source, and the size of the object and relative size of the feature to be seen. Contrast resolution relates to the ability to detect differences in densities, particularly when resolving features embodied in close density differences. Spatial resolution is interrelated particularly to contrast resolution, and refers to the ability to resolve two features very close together, e.g., two 1 mm objects only 1 mm apart. Square holes often show up as round holes due to the failure of detecting geometric shapes. Therefore, the present invention includes as alternative and additional steps thereof the use of square inserts and corresponding sub-inserts, to serve spatial resolution testing purposes just as well as would two separate objects (since both the hole and the geometry thereof may be the subject of detection, and hence testing).

Use of the varying hole or opening sizes, in a particular order and pattern, assist in the calibration procedure, since it provides a known and/or expected location of such openings. In other words, particularly in connection with the relatively smaller holes, such construction will make it easier to find them. Use of ordering of holes, in particular locations as well, in order to facilitate finding same, is an idea which is reflected in the products known as "Radiographic Penetrameters". Such products were used to determine film or picture quality, not detectability or resolution, or the ability to determine densities.

It should be well apparent to those of ordinary skill in the art that a great variety of piece shapes, dimensions, and materials, may be practiced in accordance with broader aspects of this invention. Various methodologies may be practiced as well, in keeping with the broader methods discussed above. The present aspect forming a chief concern of this invention is that the calibrator comprising an interchangeable set of pieces in accordance with this invention provide the simple and easy capability of varying size and combinations of density (including that of air and fluids) for characterizing CT system capabilities. Variations in particular sizes, shapes, densities of material, as well as variety in the assembled configurations thereof, and uses thereof as generally outlined above, are all intended to come within the spirit and scope of the present invention, which is set forth more particularly in the appended claims.

What is claimed is:

1. An industrial computerized tomography calibrator, comprising:
   a plurality of nestable, planar rings, removably received relative one another, and each respectively defining at least one opening of predetermined size situated therein, between their respective inside and outside diameters; and
   a plurality of planar inserts for being fit and removably received in said predetermined-size openings;
   wherein said rings and inserts are comprised of selected materials having known densities and dimensions;
   so that differing combinations of said rings and inserts are provided to establish predetermined density and dimensional material relationships in a given plane, for use in calibrating an industrial computer tomography system; and further wherein
   said inserts each respectively define a plurality of sub-openings of predetermined size therein, and said calibrator further includes a plurality of planar sub-inserts for being fit and removably received in said sub-openings;
   a central ring of said plurality of rings defines a disc with a generally square opening therein, and the remainder of said plurality of rings each respectively define a generally square opening and a separate circular opening therein; and
   said sub-openings and sub-inserts are generally rectangular in shape.

2. A calibrator as in claim 1, further including non-corrosive fluid of a predetermined, known density removably entrapped within a given sub-opening.

3. An industrial computerized tomography calibrator, comprising:
   a plurality of nestable, planar rings, removably received relative one another, an each respectively defining at least one opening of predetermined size situated therein, between their respective inside and outside diameters; and
   a plurality of planar inserts for being fit and removably received in said predetermined-size openings;
   wherein said rings and inserts are comprised of selected materials having known densities and dimensions;
   so that differing combinations of said rings and inserts are provided to establish predetermined density and dimensional material relationships in a given plane, for use in calibrating an industrial computer tomography system; and further
   wherein said inserts each respectively define a plurality of sub-openings of predetermined size therein, and said calibrator further includes a plurality of planar sub-inserts for being fit and removably received in said sub-openings; and
   wherein said plurality of sub-openings comprise nine sub-openings defined in each insert, said nine sub-openings being situated in a predetermined, fixed spatial pattern and having different dimensional characteristics in grouped sets of three.

4. An industrial computerized tomography calibrator, comprising:
   a plurality of nestable, planar rings, removably received relative one another, and each respectively defining at least one opening of predetermined size situated therein, between their respective inside and outside diameters; and
   a plurality of planar inserts for being fit and removably received in said predetermined-size openings;
   wherein said rings and inserts are comprised of selected materials having known densities and dimensions;
   so that differing combinations of said rings and inserts are provided to establish predetermined density and dimensional material relationships in a given plane, for use in calibrating an industrial computer tomography system; and further
   wherein said inserts each respectively define a plurality of sub-openings of predetermined size therein, and said calibrator further includes a plurality of planar sub-inserts for being fit and removably received in said sub-openings; and
   wherein the thickness of said planar rings, said planar inserts, and said planar sub-inserts is 10 mm, and all of such planar members comprise material having a known, fixed density in a range of from near 0 to 10 gm/cc.

5. A calibrator as in claim 4, wherein said planar members comprise one of aluminum, copper, and stainless steel.

6. A device to aid in the image focusing of a computer tomography system having computer means with adjustable variables for generating an image from exposure detection data gathered with such system, said device including:
   a plurality of generally planar mother block means, of predetermined size, thickness, and density, for being removably associated with one another, and having primary openings therein, for establishing a dimensionally known planar pattern of such primary openings;
   a plurality of generally planar insert means, of predetermined size, thickness, and density, and for being removably received in said mother block means primary openings, for filling same; and
   wherein said mother block means includes a plurality of nestable concentric members and one central disc, each having at least one primary opening therein;
   so that selected planar configurations of varying combinations of known sizes and densities are provided, to permit adjustment of the system computer means variables for optimum image detection and image contrast and spatial resolution.

7. A device as in claim 6, wherein said concentric members are annular, and said primary openings thereof are respectively situated between the inside and outside diameters of each such annular member.

8. A device as in claim 6, wherein said primary openings are rectangular, and said insert means are correspondingly rectangular for selectively fitting therein.

9. A device as in claim 6, wherein said primary openings are circular, and said insert means are correspondingly circular for selectively fitting therein.

10. A device as in claim 6, wherein said densities are in a range of from near 0 to 10 gm/cc.

11. A device as in claim 6, wherein said predetermined thickness of said mother block means and said insert means is 10 mm.

12. A device as in claim 6, wherein said insert means comprise non-corrosive fluids received within a given mother block means primary opening.

13. A device to aid in the image focusing of a computer tomography system having computer means with adjustable variables for generating an image from exposure detection data gathered with such system, said device including:

a plurality of generally planar mother block means, of predetermined size, thickness, and density, for being removably associated with one another, and having primary openings therein, for establishing a dimensionally known planar pattern of such primary openings; and a plurality of generally planar insert means, of predetermined size, thickness, and density, and for being removably received in said mother block means primary openings, for filling same;

so that selected planar configurations of varying combinations of known sizes and densities are provided, to permit adjustment of the system computer means variables for optimum image detection and image contrast and spatial resolution; and wherein said insert means further define secondary openings therein, and said device further includes secondary inserts of predetermined size, thickness, and density, for being removably received in said secondary openings; and wherein said mother block means includes four two-inch wide nested rings varying from a maximum diameter of fourteen inches to a central ring of two inches in diameter, and further wherein said insert means comprise either circular members having 25 mm in diameter or square members having 25 mm on each side, with said secondary openings thereof comprising squares of varying sizes with sides in a range of from 2 mm to 0.5 mm.

14. A device as in claim 13, wherein said secondary inserts comprise non-corrosive fluids received within a given insert means secondary opening.

15. A set of interchangeable pieces for use in focusing the level of detectability and the contrast and spatial resolution of a computer tomography system having settable variables for adjusting effective image detectability and resolution of the system, said pieces including a plurality of nestable, generally planar mother rings, each ring having at least one predetermined opening within its respective circumference for the receipt of planar inserts of predetermined sizes in such openings, and said pieces further including a plurality of removable planar inserts for being received in said mother ring openings, wherein said mother rings and inserts are comprised of materials having known densities, so that different configurations of materials of known sizes and combinations of densities are provided generally in a given plane to be scanned with the computer tomography system for focusing of such system through adjustment of the settable variables thereof; and wherein said planar inserts each define plural openings therein of predetermined, fixed sizes and relative spacing, and said set of pieces further includes a plurality of sub-inserts for being received in said planar insert openings, so that various configurations of said interchangeable pieces are resolved into selected, progressively smaller orders of magnitude through use of said plurality of sub-inserts;

said planar mother rings have an outside diameter preferably in a range of from two to fourteen inches, and said predetermined openings therein are either circular with a radius of about 25 mm, or square with side lengths of about 25 mm;

said planar inserts are either generally circular with a radius of 25 mm, or square with side lengths of 25 mm, and said insert openings are generally square with side lengths in a range of from 2 mm to 0.5 mm; and said mother rings, planar inserts, and sub-inserts have about the same predetermined thickness.

16. A set of interchangeable pieces as in claim 15, wherein said predetermined thickness is 10 mm.

17. A set of interchangeable pieces as in claim 15, wherein said pieces are respectively comprised of one of aluminum, copper, stainless steel, carbon, carbon composite, a non-corrosive fluid, and air.

18. A set of interchangeable pieces for use in focusing the level of detectability and the contrast and spatial resolution of a computer tomography system having settable variables for adjusting effective image detectability and resolution of the system, said pieces including a plurality of nestable, generally planar mother rings, each ring having at least one predetermined opening within its respective circumference for the receipt of planar inserts of predetermined sizes in such openings, and said pieces further including a plurality of removable planar inserts for being received in said mother ring openings, wherein said mother rings and inserts are comprised of materials having known densities, so that different configurations of materials of known sizes and combinations of densities are provided generally in a given plane to be scanned with the computer tomography system for focusing of such system through adjustment of the settable variables thereof; and wherein said planar inserts each define plural openings therein of predetermined, fixed sizes and relative spacing, and said set of pieces further includes a plurality of sub-inserts for being received in said planar insert openings, so that various configurations of said interchangeable pieces are resolved into selected, progressively smaller orders of magnitude through use of said plurality of sub-inserts;

wherein the predetermined density of said mother rings, planar inserts, and sub-inserts is in a range of from 2 to 10 gm/cc.

19. A set of interchangeable pieces for use in focusing the level of detectability and the contrast and spatial resolution of a computer tomography system having settable variables for adjusting effective image detectability and resolution of the system, said pieces including a plurality of nestable, generally planar mother rings, each ring having at least one predetermined opening within its respective circumference for the receipt of planar inserts of predetermined sizes in such openings, and said pieces further including a plurality of removable planar inserts for being received in said mother ring openings, wherein said mother rings and inserts are comprised of materials having known densities, so that different configurations of materials of known sizes and combinations of densities are provided generally in a given plane to be scanned with the computer tomography system for focusing of such system through adjustment of the settable variables thereof; and wherein said planar inserts each define plural openings therein of predetermined, fixed sizes and relative spacing, and said set of pieces further includes a plurality of sub-inserts for being received in said planar insert openings, so that various configurations of said interchangeable pieces are resolved into selected, progressively smaller orders of magnitude through use of said plurality of sub-inserts;

wherein there are a total of four mother rings, seven planar inserts, and sixty-three sub-inserts, for a total of seventy-four pieces comprising a complete set of said interchangeable pieces.

20. A method of focusing a computer tomography system of the type having a radiation source for exposing an object to be scanned, an exposure support surface for supporting an object to be scanned, detector means for detecting scan information, and computer means with operating variables for processing scan information into images, said method including:

providing a set of interchangeable pieces, each piece comprising a given material of generally known density and dimensions, said set of pieces including a plurality of nestable mother rings, and inserts for removable selected association with each of said mother rings;

assembling at least certain of said pieces into a given configuration thereof, with such configuration being received on the computer tomography system exposure support surface;

operating the computer tomography system for exposing the assembled configuration of pieces; and processing detected scan information into images, including adjusting the computer means operating variables so as to obtain optimum image quality based on the known configuration of certain densities and dimensions provided with the assembled pieces.

21. A method as in claim 20, wherein:

said mother rings include primary openings for receipt of said inserts, and further wherein said inserts include secondary openings therein for receipt of sub-inserts; and said assembling step includes selected inclusion of sub-inserts of known density and dimensions in the insert secondary openings.

22. A method as in claim 21, wherein said assembling step includes the step of selecting use of given mother rings and sub-inserts based on the relative dimensions thereof in relation to the size of an intended object to be scanned with the system and the anticipated size of defects in such intended object, generally such that the dimensions of the largest mother ring selected are at least as large as the intended object to be scanned, and the dimensions of the smallest sub-insert selected are no larger than the smallest anticipated defect in such intended object.

23. A method as in claim 21, wherein said assembling step further includes selectively entrapping air or non-corrosive fluids of known density in predetermined areas of the assembled configuration, for further variety in the known density and location of material to be scanned.

24. A method as in claim 21, wherein said primary and secondary openings and said inserts and sub-inserts comprise corresponding selected geometric shapes, including circular shapes to selectively avoid artifact stimulation, and rectangular shapes to selectively stimulate artifact generation, whereby selective use of rectangular shapes permits simultaneous testing of geometry and density resolution with a single opening/insert pair.

25. A method as in claim 20, wherein:

the interchangeable pieces are generally planar and have respective thicknesses which are greater than the usual thickness of a given plane to be scanned with the computer tomography system; and the assembling step includes the stacking of at least two thicknesses of some of the interchangeable pieces of the same or of differing densities to permit testing of the level of system rejection of scan information from adjacent planar locations, outside the intended given plane to be scanned.

26. A method as in claim 20, further including the step of placing a test piece of known size and density on the computer tomography system exposure support surface, outside the assembled configuration of said interchangeable pieces, to permit monitoring of drift in relative density indications from one processed image to another, by not changing such test piece between formation of such images.

* * * * *